United States Patent [19]

Matsumoto et al.

[11] Patent Number: 4,530,916
[45] Date of Patent: Jul. 23, 1985

[54] CATALYST FOR USE IN A METHACRYLIC ACID PROCESS

[75] Inventors: Mutsumi Matsumoto; Hideki Sugi, both of Takasaki, Japan

[73] Assignee: Nippon Kayaku Kabushiki Kaisha, Tokyo, Japan

[21] Appl. No.: 555,674

[22] Filed: Nov. 28, 1983

Related U.S. Application Data

[62] Division of Ser. No. 95,668, Nov. 19, 1979, Pat. No. 4,467,113.

[30] Foreign Application Priority Data

Dec. 13, 1978 [JP] Japan .................. 53-153158

[51] Int. Cl.³ .................. B01J 27/14; B01J 21/02
[52] U.S. Cl. .................. 502/209; 502/205; 502/206; 502/210; 502/212
[58] Field of Search .............. 502/205, 206, 209, 210, 502/212

[56] References Cited

U.S. PATENT DOCUMENTS

| | | | |
|---|---|---|---|
| 3,875,220 | 4/1975 | White et al. | 502/206 X |
| 4,001,316 | 1/1977 | Ishimi | 502/200 X |
| 4,172,051 | 10/1979 | Matsumoto et al. | 502/209 |
| 4,178,464 | 12/1979 | Sakamoto et al. | 502/209 X |
| 4,180,678 | 12/1979 | Wada et al. | 502/209 X |
| 4,273,676 | 6/1981 | Matsumoto et al. | 502/209 |
| 4,444,907 | 4/1984 | Ohdan et al. | 502/209 X |

FOREIGN PATENT DOCUMENTS 1473035  5/1977  United Kingdom .
1492185 11/1977  United Kingdom .

OTHER PUBLICATIONS

Inorganic Chemistry, vol. 7, No. 3, Mar. 1968, pp. 437–441.

*Primary Examiner*—D. E. Gantz
*Assistant Examiner*—William G. Wright
*Attorney, Agent, or Firm*—Henry C. Nields

[57] ABSTRACT

A catalyst having heteropoly-acid structure and the general formula:

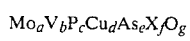

$$Mo_aV_bP_cCu_dAs_eX_fO_g$$

wherein, X represents one or more elements selected from the group consisting of tin, lead, cerium, cobalt, iron, zirconium, thorium, tungsten, germanium, nickel, rhenium, bismuth, antimony, chromium, boron, magnesium, silver, aluminum, zinc and titanium and a, b, c, d, e, f and g represent the atomic ratio of the elements where, a is 10,
b is a number of 3 or less than 3 excluding 0,
c is a number of 0.5 to 6,
d is a number of 3 or less than 3 excluding 0,
e is a number of 3 or less than 3 excluding 0,
f is a number of 0 to 3,
g is a number determined depending on the valency and atomic ratio of other elements.

There is also provided a process for producing methacrylic acid by oxidizing methacrolein with molecular oxygen or molecular oxygen-containing gas in the presence of the catalyst defined above.

3 Claims, No Drawings

CATALYST FOR USE IN A METHACRYLIC ACID PROCESS

This application is a division of application Ser. No. 095,668, filed Nov. 19, 1979, U.S. Pat. No. 4,467,113.

DETAILED DESCRIPTION OF THE INVENTION

This invention relates to a process for producing methacrylic acid by the oxidation of methacrolein characterized by the use of a new catalyst which has high activity, high selectivity, as well as very long catalyst life.

This invention relates as well to the catalyst.

Although various catalyst systems have recently been proposed for the catalytic oxidation of methacrolein in vapor phase, industrial practice for the oxidation of methacrolein has not yet been attained in contrast to the oxidation of acrolein for the production of acrylic acid. The difficulty arises, it is considered, from the facts that yield of the end product is not so high as in the production of acrylic acid, the life of most catalysts is too short to maintain stable catalytic activity for a long time and the like.

Most of the catalysts proposed for catalytic oxidation of methacrolein in vapor phase are those having molybdenumphosphorus as the major component, and structurally they are considered to be phosphomolybdates, for instance, mainly ammonium or alkali salts of heteropolyacid thereof.

However, the largest disadvantage of these catalysts is their short life as a catalyst, and in the long run of reaction the decomposition of the structure of heteropolyacid salt slowly occurs and crystal growth of $MoO_3$ is found through X-ray diffraction analysis, accompanying the reduction of its catalytic activity. Accordingly, such catalysts do not have sufficiently long life for industrial use, and in order to maintain the catalytic activity for a long time in such a catalytic system it is inevitable under the existing circumstances to choose the extremely mild reaction conditions far remote from economical demand.

Further, U.S. Pat. Nos. 3,875,220 and 4,001,316 disclose a catalyst for the oxidation of methacrolein. However, the yield of methacrylic acid obtained in the Examples of these patents is not good.

Furthermore, we, as the members of inventors, published DOS 2739779 where Mo-P-V-Al-Y-O (Y is optional and represents Cu etc.) catalyst having heteropoly-acid structure is used for the oxidation of methacrolein. This catalyst is stable. The yield of methacrylic acid in this publication is high, but is not sufficient. We, as the members of inventors, filed U.S. patent application Ser. No. 948,761 now U.S. Pat No. 4,273,676 concerning Mo-P-V-Cu-Z-O (Z is optional and represents tin etc.) catalyst having heteropoly-acid structure and a process for producing methacrylic acid by oxidizing methacrolein in the presence of the catalyst. This catalyst has high activity and high selectivity. Further, this catalyst is very stable and, therefore, has a very long catalyst life.

We, the inventors of the present application, made further study to improve the above catalyst, and accomplished this invention. The catalyst according to this invention can produce methacrylic acid from methacrolein at a high yield and in a stabilized state for a long time.

This invention relates to a process for producing methacrylic acid by oxidizing methacrolein with molecular oxygen or molecular oxygen-containing gas in the vapor phase characterized by the use of a catalyst having heteropoly-acid structure and the general formula:

$$Mo_a V_b P_c Cu_d As_e X_f O_g$$

wherein Mo, V, P, Cu, As and O represent respectively molybdenum, vanadium, phosphorus, copper, arsenic and oxygen, X represents one or more elements selected from the group consisting of tin, lead, cerium, cobalt, iron, zirconium, thorium, tungsten, germanium, nickel, rhenium, bismuth, antimony, chromium, boron, magnesium, silver, aluminum, zinc and titanium and a, b, c, d, e, f and g represent the atomic ratio of the elements where, a is 10,
b is a number of 3 or less than 3 excluding 0 and, preferably, 0.5 to 2,
c is a number of 0.5 to 6 and, preferably, 0.5 to 3,
d is a number of 3 or less than 3 excluding 0 and, preferably, 0.01 to 1.0,
e is a number of 3 or less than 3 excluding 0 and, preferably, 0.01 to 1.0,
f is a number of 0 to 3 and, preferably, 0 to 1.0,
g is a number determined depending on the valency and atomic ratio of other elements and is usually a number of 32 to 90.

This invention relates as well to the catalyst defined above.

Particularly preferred component X includes tin, thorium, cerium, tungsten, germanium, rhenium, bismuth, antimony, boron and aluminum.

The foregoing catalyst used in this invention contains various elements and has heteropolyacid structure as shown by the characteristic peaks of X-ray diffraction at 2θ=8.0°, 8.9°, 9.3° and the like. While the basic structure of the catalyst is phosphovanadomolybdic acid, other elements incorporated therein are considered to contribute to the improvements in the catalytic activity and selectivity, as well as in the stability of the structure by partially replacing the constituent elements in the phosphovanadomolybdic acid and being incorporated into the structure of the heteropoly-acid.

The catalyst of this invention is water soluble since it has heteropoly-acid structure as described above. It may additionally contain water insoluble components such as oxides of the constituent elements but they have no substantial effects on the performance of the catalyst of this invention.

It is considered that, as in the conventional case, the catalyst of this invention is also in the reduced form under the reaction condition by being reduced with the feed gas containing methacrolein at the early stage of the reaction. The reduced form can be obtained also by using reducible starting materials for the constituent elements of the catalyst, adding the reductant when preparing the catalyst or treating the catalyst with a reducible gas.

The catalyst of this invention is excellent for the industrial use since it has high activity, high selectivity, as well as very long catalyst life. Further, according to this invention, the reaction can be conducted at a high space velocity, because the increace in the space velocity has no substantial effects on the results of the reaction where the catalyst of this invention is employed. The catalyst of this invention is water soluble, which provides additional advantages in that it can easily be carried on a carrier and regenerated also with ease by dissolving it again in water after being deactivated in a long use for the reaction.

While the catalyst of this invention can be prepared by general methods for preparing usual heteropolyacids, it should particularly be noted to avoid the formation of a heteropoly-acid ammonium salt structure in the resultant catalyst.

The catalyst of this invention can be prepared, for example, in the following manner. The catalyst of this invention can be prepared by reacting the starting materials of the constituent elements in water or in an organic solvent, converting the reaction product into the corresponding acid when it is ammonium salt, extracting the reaction product if necessary, and evaporating to dryness. The conversion of ammonium salt into the corresponding acid can be carried out through conventional ways, for example, by ether extraction from an acidic aqueous solution, ion exchange process and the like. The extraction of the reaction product can be carried out by using a suitable organic solvent such as ether.

Particularly preferred preparation methods include those such as dispersing or dissolving the starting material, for example, oxides or phosphates of the constituent elements into water, reacting the same under heating while optionally adding hydrogen peroxide, removing insoluble component if necessary, and then evaporating the solution to dryness, or reacting phosphovanadomolybdic acid with oxides, phosphates, sulfates and the likes of other constituent elements.

Various substances can be used as the starting material for the constituent elements of the catalyst, so long as they are treated in such a process as resulting in a catalyst of heteropoly-acid structure but not of ammonium salt structure.

The starting materials usable for the molybdenum component include, for example molybdenum trioxide, molybdic acid or its salt, heteromolybdic acid or its salts, molybdenum metal and the like.

The starting materials usable for the phosphorous component include orthophosphoric acid, phosphorous acid, hypophosphorous acid or the salts thereof, diphosphorus pentoxide and the like.

The starting materials usable for the vanadium component include vanadium pentoxide, vanadium oxalate, vanadium sulfate, vanadic acid or its salts, vanadium metal and the like.

The starting materials usable for the copper component include copper oxide, copper phosphate, copper sulfate, copper nitrate, copper molybdate, copper metal and the like.

The starting materials usable for the arsenic component include arsenic oxide, orthoarsenic acid, metaarsenic acid, pyroarsenic acid or their salts and the like.

The starting materials usable for the component X include corresponding oxides, phosphates, nitrates, sulfates, carbonates, molybdates, metals of the elements X and the like.

While the catalyst according to this invention exhibits high catalytic activity as it is, preferable effects such as improvements in thermal stability and catalyst life and increase in yield of methacrylic acid can be expected by carrying it on a suitable carrier. Preferred carriers include silicon carbide, aluminum powder, diatomaceous earth, titanium oxide α-alumina etc. The active carriers which react with heteropoly-acid are not preferable.

The calcination process which is required in most cases is not required when preparing the catalyst of this invention. Therefore, the catalyst of this invention can be prepared with ease and the price of the catalyst can be reduced.

The reactants used for the oxidation reaction in this invention are methacrolein and molecular oxygen or molecular oxygen-containing gas, wherein the molar ratio of oxygen to methacrolein preferably lies between 0.5 and 10 and, more preferably, between 2 and 5.

It is preferable to add water vapor to the feed gas in an amount between 1 and 20 and, more preferably, between 2 and 15 by molar ratio based on methacrolein.

The feed gas may further contain other inert gases, for example, nitrogen, carbon dioxide, saturated hydrocarbon or the like. The effluent gas containing methacrolein obtained by catalytic oxidation of isobutylene or tertiary butanol can be used as the feed gas.

The reaction temperature is preferably between 200°–380° C. and, more preferably, 250°–350° C.

The amount of the feed gas is preferably between 100 and 5,000 $hr^{-1}$ and, more preferably, between 500 and 3,000 $hr^{-1}$ as space velocity (SV) based on the NTP standard. Since the increase in the space velocity (SV) has no substantial effect on the results of the reaction where the catalyst of this invention is employed, the reaction can be conducted at a high space velocity.

While the reaction of this invention can be effected at a pressure either above or below the atmospheric pressure, it is suitably effected generally at a pressure near the atmospheric pressure. The preferred pressure for the reaction in this invention lies between 1 and 5 atm.

The reaction of this invention can be effected in any desired type of reactor such as of a fixed bed, a fluidized bed or a moving bed type.

In the following examples, no particular references are made to the details of oxygen in the catalyst composition since they are determined in accordance with the atomic ratio and valency of other elements.

The conversion of methacrolein, the yield of methacrylic acid and the selectivity to methacrylic acid are defined as follows:

Conversion of methacrolein (%) =

$$\frac{\text{methacrolein reacted (mol)}}{\text{methacrolein supplied (mol)}} \times 100$$

Yield of methacrylic acid (%) =

$$\frac{\text{methacrylic acid resulted (mol)}}{\text{methacrolein supplied (mol)}} \times 100$$

Selectivity to methacrylic acid (%) =

$$\frac{\text{yield of methacrylic acid}}{\text{conversion of methacrolein}} \times 100$$

EXAMPLE 1

100 g of molybdenum trioxide, 6.3 g of vanadium pentoxide, 1.1 g of copper oxide, 8.0 g of orthophosphoric acid and 1.8 g of pyroarsenic acid were dispersed or dissolved into 1000 ml of deionized water. The resultant mixture was boiled and refluxed with stirring for about 6 hours to produce a clear orange red solution. It was evaporated to dryness on a hot bath. The dried product thus obtained (catalyst) had a composition: $Mo_{10}V_1P_1Cu_{0.2}As_{0.2}$ and were confirmed to be heteropoly-acid by the observation of diffraction peaks at $2\theta = 8.0°$, 8.9°, 9.3° and the like through X-ray diffraction. It was ground to 24-48 mesh and then charged into a tubular reactor made of Pyrex glass of 18 mm in inside diameter and the reactor was immersed in a fluidized bath. The feed gas of a composition wherein methacrolein: oxygen:nitrogen:water vapour=1:2.5:14:7 (in molar ratio) was passed through the tubular reactor at $SV = 1,600$ hr$^{-1}$ (NTP standard) and subjected to oxidation reaction at a reaction temperature of 320° C. for 120 days. The results are shown in Table 1.

After the reaction of 120 days, X-ray diffraction analysis of the catalyst was made and it was confirmed that molybdenum trioxide had not been formed and the structure of the catalyst had not changed.

EXAMPLE 2

100 g of molybdenum trioxide, 6.3 g of vanadium pentoxide, 1.1 g of copper oxide, 8.0 g of orthophosphoric acid, 1.8 g of pyroarsenic acid and 2.1 g of tin oxide were used as the starting material to prepare dried product (catalyst): $Mo_{10}V_1P_1Cu_{0.2}As_{0.2}Sn_{0.2}$ in the same procedure as in Example 1. The dried products thus obtained were confirmed to be heteropoly-acid by the observation of diffraction peaks at $2\theta = 8.0°$, 8.9°, 9.3° and the like through X-ray diffraction.

A continuous reaction was carried out for 30 days using the above catalyst under the same conditions as in Example 1. The results are as shown in Table 1.

After the reaction of 30 days, X-ray diffraction analysis of the catalyst was made and it was confirmed that the structure of the catalyst had not changed.

EXAMPLES 3-21

2.1 g of tin oxide in Example 2 was replaced in each of the examples with 3.2 g of trilead tetroxide, 2.4 g of cerium oxide, 1.1 g of tricobalt tetroxide, 1.1 g of iron oxide, 1.7 g of zirconium oxide, 3.7 g of thorium oxide, 3.2 g of tungsten trioxide, 1.5 g of germanium oxide, 1.0 g of nickel oxide, 3.4 g of rhenium heptoxide, 3.2 g of bismuth oxide, 2.0 g of antimony trioxide, 1.4 g of chromium trioxide, 0.9 g of boric acid, 0.6 g of magnesium oxide, 1.6 g of silver oxide, 0.7 g of aluminum oxide, 1.1 g of zinc oxide, and 1.1 g of titanium oxide respectively and dried products having compositions as shown in Table 1 were obtained. The dried products thus obtained were confirmed to be heteropoly-acid by the observation of diffraction peaks at $2\theta = 8.0°$, 8.9°, 9.3° and the like through X-ray diffraction.

A series of continous reactions were conducted using the above catalysts under the same reaction conditions as in Example 1. The results are as shown in Table 1.

After the reaction of 30 days, X-ray diffraction analysis of the catalysts was made and it was confirmed that the structure of the catalysts had not changed.

TABLE 1

| Example | Catalyst Composition | Time on Stream (days) | Reaction Temperature (°C.) | Conversion of methacrolein (%) | Selectivity to methacrylic acid (%) | Yield of methacrylic acid (%) |
|---|---|---|---|---|---|---|
| 1 | $Mo_{10}V_1P_1Cu_{0.2}As_{0.2}$ | 1 | 320 | 93.4 | 83.6 | 78.1 |
|   |   | 120 | 320 | 93.5 | 83.9 | 78.4 |
| 2 | $Mo_{10}V_1P_1Cu_{0.2}As_{0.2}Sn_{0.2}$ | 1 | 320 | 91.2 | 83.9 | 76.5 |
|   |   | 30 | 320 | 92.1 | 83.3 | 76.7 |
| 3 | $Mo_{10}V_1P_1Cu_{0.2}As_{0.2}Pb_{0.2}$ | 1 | 330 | 90.4 | 82.2 | 74.3 |
|   |   | 30 | 330 | 91.2 | 83.3 | 76.7 |
| 4 | $Mo_{10}V_1P_1Cu_{0.2}As_{0.2}Ce_{0.2}$ | 1 | 315 | 92.5 | 81.5 | 75.4 |
|   |   | 30 | 315 | 92.2 | 81.8 | 75.4 |
| 5 | $Mo_{10}V_1P_1Cu_{0.2}As_{0.2}Co_{0.2}$ | 1 | 312 | 95.7 | 80.9 | 77.4 |
|   |   | 30 | 312 | 96.0 | 80.8 | 77.6 |
| 6 | $Mo_{10}V_1P_1Cu_{0.2}As_{0.2}Fe_{0.2}$ | 1 | 315 | 94.1 | 82.1 | 77.3 |
|   |   | 30 | 315 | 94.7 | 82.1 | 77.7 |
| 7 | $Mo_{10}V_1P_1Cu_{0.2}As_{0.2}Zr_{0.2}$ | 1 | 317 | 93.8 | 83.7 | 78.5 |
|   |   | 30 | 317 | 93.1 | 83.9 | 78.1 |
| 8 | $Mo_{10}V_1P_1Cu_{0.2}As_{0.2}Th_{0.2}$ | 1 | 320 | 92.2 | 82.4 | 76.0 |
|   |   | 30 | 320 | 92.8 | 82.1 | 76.2 |
| 9 | $Mo_{10}V_1P_1Cu_{0.2}As_{0.2}W_{0.2}$ | 1 | 325 | 90.4 | 83.7 | 75.7 |
|   |   | 30 | 325 | 90.1 | 84.0 | 75.7 |
| 10 | $Mo_{10}V_1P_1Cu_{0.2}As_{0.2}Ge_{0.2}$ | 1 | 320 | 92.0 | 82.8 | 76.2 |
|   |   | 30 | 320 | 92.7 | 82.6 | 76.6 |
| 11 | $Mo_{10}V_1P_1Cu_{0.2}As_{0.2}Ni_{0.2}$ | 1 | 320 | 94.9 | 82.7 | 78.5 |
|   |   | 30 | 320 | 94.4 | 83.4 | 78.7 |
| 12 | $Mo_{10}V_1P_1Cu_{0.2}As_{0.2}Re_{0.2}$ | 1 | 320 | 94.1 | 80.5 | 75.8 |
|   |   | 30 | 320 | 93.7 | 81.1 | 76.0 |
| 13 | $Mo_{10}V_1P_1Cu_{0.2}As_{0.2}Bi_{0.2}$ | 1 | 320 | 96.0 | 81.3 | 78.0 |
|   |   | 30 | 320 | 95.5 | 81.7 | 78.0 |
| 14 | $Mo_{10}V_1P_1Cu_{0.2}As_{0.2}Sb_{0.2}$ | 1 | 330 | 90.9 | 84.0 | 76.4 |
|   |   | 30 | 330 | 91.5 | 83.8 | 76.7 |
| 15 | $Mo_{10}V_1P_1Cu_{0.2}As_{0.2}Cr_{0.2}$ | 1 | 320 | 91.3 | 83.6 | 76.3 |
|   |   | 30 | 320 | 90.6 | 83.3 | 75.5 |
| 16 | $Mo_{10}V_1P_1Cu_{0.2}As_{0.2}B_{0.2}$ | 1 | 320 | 89.9 | 83.7 | 75.2 |
|   |   | 30 | 320 | 90.3 | 83.1 | 75.0 |
| 17 | $Mo_{10}V_1P_1Cu_{0.2}As_{0.2}Mg_{0.2}$ | 1 | 320 | 92.4 | 83.4 | 77.1 |
|   |   | 30 | 320 | 92.3 | 83.7 | 77.3 |
| 18 | $Mo_{10}V_1P_1Cu_{0.2}As_{0.2}Ag_{0.2}$ | 1 | 330 | 95.3 | 81.4 | 77.6 |
|   |   | 30 | 330 | 95.4 | 81.7 | 77.9 |
| 19 | $Mo_{10}V_1P_1Cu_{0.2}As_{0.2}Al_{0.2}$ | 1 | 330 | 92.7 | 83.0 | 76.9 |
|   |   | 30 | 330 | 91.9 | 83.0 | 76.3 |
| 20 | $Mo_{10}V_1P_1Cu_{0.2}As_{0.2}Zn_{0.2}$ | 1 | 320 | 91.4 | 82.7 | 75.6 |
|   |   | 30 | 320 | 92.1 | 82.8 | 76.3 |
| 21 | $Mo_{10}V_1P_1Cu_{0.2}As_{0.2}Ti_{0.2}$ | 1 | 330 | 93.3 | 80.9 | 75.5 |
|   |   | 30 | 330 | 92.9 | 81.6 | 75.8 |

EXAMPLES 22-25

The dried products as shown in Table 2 were prepared as in Example 1 and were confirmed to be heteropoly-acid by X-ray diffraction analysis.

The continuous reactions were conducted using the above catalysts in the same reaction conditions as in Example 1. The results are shown in Table 2.

After the reaction of 30 days, X-ray diffraction analysis of the catalysts was made and it was confirmed that the structure of the catalysts had not changed.

TABLE 2

| Example | Catalyst Composition | Time on Stream (days) | Reaction Temperature (°C) | Conversion of methacrolein (%) | Selectivity to methacrylic acid (%) | Yield of methacrylic acid (%) |
|---|---|---|---|---|---|---|
| 22 | $Mo_{10}V_1P_1Cu_{0.2}As_{0.2}Sn_{0.1}Pb_{0.1}$ | 1 | 320 | 93.4 | 82.4 | 77.0 |
|  |  | 30 | 320 | 92.8 | 82.9 | 76.9 |
| 23 | $Mo_{10}V_1P_1Cu_{0.2}As_{0.2}Ge_{0.1}Ni_{0.1}$ | 1 | 320 | 94.0 | 83.1 | 78.1 |
|  |  | 30 | 320 | 93.9 | 83.3 | 78.2 |
| 24 | $Mo_{10}V_1P_1Cu_{0.2}As_{0.2}Bi_{0.1}Cr_{0.1}$ | 1 | 320 | 94.8 | 81.1 | 76.7 |
|  |  | 30 | 320 | 94.8 | 81.6 | 77.4 |
| 25 | $Mo_{10}V_1P_1Cu_{0.2}As_{0.2}Al_{0.1}Ti_{0.1}$ | 1 | 320 | 92.9 | 80.8 | 75.1 |
|  |  | 30 | 320 | 93.6 | 81.0 | 75.8 |

EXAMPLES 26-31

The dried products as shown in Table 3 were prepared as in Example 1 and were confirmed to be heteropoly-acid by X-ray diffraction analysis.

The continuous reactions were conducted using the above catalysts in the same reaction conditions as in Example 1. The results are shown in Table 3.

After the reaction of 30 days, X-ray diffraction analysis of the catalysts was made and it was confirmed that the structure of the catalysts had not changed.

TABLE 3

| Example | Catalyst Composition | Time on Stream (days) | Reaction Temperature (°C) | Conversion of methacrolein (%) | Selectivity to methacrylic acid (%) | Yield of methacrylic acid (%) |
|---|---|---|---|---|---|---|
| 26 | $Mo_{10}V_{1.5}P_1Cu_{0.3}As_{0.1}$ | 1 | 345 | 91.3 | 80.1 | 73.1 |
|  |  | 30 | 345 | 92.0 | 80.3 | 73.9 |
| 27 | $Mo_{10}V_1P_3Cu_{0.5}As_{0.1}Sn_{0.1}$ | 1 | 340 | 87.1 | 75.5 | 65.8 |
|  |  | 30 | 340 | 87.0 | 75.6 | 65.8 |
| 28 | $Mo_{10}V_{0.5}P_1Cu_{0.05}As_{0.05}Sn_{0.2}$ | 1 | 320 | 90.0 | 75.8 | 68.2 |
|  |  | 30 | 320 | 89.8 | 75.6 | 67.9 |
| 29 | $Mo_{10}V_{1.5}P_1Cu_{1.0}As_{0.2}Ni_{0.2}$ | 1 | 330 | 91.4 | 78.4 | 71.7 |
|  |  | 30 | 330 | 90.2 | 77.7 | 70.1 |
| 30 | $Mo_{10}V_1P_2Cu_{0.2}As_{0.1}Ge_{1.0}$ | 1 | 335 | 92.7 | 80.5 | 74.6 |
|  |  | 30 | 335 | 92.3 | 81.0 | 74.8 |
| 31 | $Mo_{10}V_1P_{0.5}Cu_{0.3}As_{1.0}Ge_{0.5}$ | 1 | 340 | 87.5 | 79.9 | 69.9 |
|  |  | 30 | 340 | 87.8 | 79.2 | 69.5 |

EXAMPLES 32-33

With the use of the catalyst of Example 6 the oxidation of methacrolein was carried out in a similar manner as in Example 1 except that the space velocity (SV) was changed. The results are shown in Table 4. These results show that the increase in the space velocity (SV) has no substantial effect on the results of the reaction.

TABLE 4

| Example | Catalyst Composition | SV (hr$^{-1}$) | Reaction temperature (°C) | Conversion of methacrolein (%) | Selectivity to methacrylic acid (%) | Yield of methacrylic acid (%) |
|---|---|---|---|---|---|---|
| 32 | $Mo_{10}V_1P_1Cu_{0.2}As_{0.2}Fe_{0.2}$ | 800 | 290 | 94.2 | 82.2 | 77.4 |
| 33 | $Mo_{10}V_1P_1Cu_{0.2}As_{0.2}Fe_{0.2}$ | 3600 | 335 | 93.8 | 81.7 | 76.6 |

COMPARISON EXAMPLE 1

28% ammonium hydroxide aqueous solution was added to the clear orange red solution obtained in Example 1 (pH ≈ 1.0) to adjust pH to 5.3. After evaporating the solution to dryness, the dried product was ground to 24-48 mesh and calcined in air at 380° C. for 8 hours. The catalyst prepared had a composition: $(NH_4)_{1.5}Mo_{10}V_1P_1Cu_{0.2}As_{0.2}$ and the formation of the ammonium salt of heteropoly-acid was confirmed from X-ray diffraction and IR absorption spectrum. A similar continuous reaction was conducted using the above catalyst. The results are shown in Table 5.

TABLE 5

| Comparison Example | Catalyst Composition | Time on Stream (days) | Reaction Temperature (°C) | Conversion of methacrolein (%) | Selectivity to methacrylic acid (%) | Yield of methacrylic acid (%) |
|---|---|---|---|---|---|---|
| 1 | $(NH_4)_{1.5}Mo_{10}V_1P_1Cu_{0.2}As_{0.2}$ | 1 | 320 | 90.1 | 82.1 | 74.0 |
|  |  | 15 | 320 | 77.8 | 76.2 | 59.3 |

What is claimed is:
1. A catalyst having heteropoly-acid structure and the general formula:

$$Mo_aV_bP_cCu_dAs_eX_fO_g$$

wherein Mo, V, P, Cu, As and O represent respectively molybdenum, vanadium, phosphorus, copper, arsenic and oxygen, X represents one or more elements selected from the group consisting of tin, lead, cerium, cobalt, iron, zirconium, thorium, tungsten, germanium, nickel, rhenium, bismuth, antimony, chromium, boron, magnesium, silver, aluminum, zinc and titanium and a, b, c, d, e, f and g represent the atomic ratio of the elements where, a is 10, b is a number of 3 or less than 3 excluding 0, c is a number of 0.5 to 6, d is a number of 3 or less than 3 excluding 0, e is a number of 3 or less than 3 excluding 0, f is a number of 0 to 3, g is a number determined depending on the valency and atomic ratio of other elements.

2. The catalyst of claim 1, where a is 10, b is a number of 0.5 to 2, c is a number of 0.5 to 3, d is a number of 0.01 to 1.0, e is a number of 0.01 to 1.0, f is a number of 0 to 1.0.

3. The catalyst of claim 1, wherein X represents one or more elements selected from the group consisting of tin, thorium, cerium, tungsten, germanium, rhenium, bismuth, antimony, boron, and aluminum.

* * * * *